United States Patent [19]
Buck et al.

[11] Patent Number: 6,004,280
[45] Date of Patent: Dec. 21, 1999

[54] GUIDING SHEATH HAVING THREE-DIMENSIONAL DISTAL END

[75] Inventors: Jerrick C. Buck, Miami; Cesar L. Silva, Pembroke Pines, both of Fla.

[73] Assignee: Cordis Corporation, Miami Lakes, Fla.

[21] Appl. No.: 09/112,463

[22] Filed: Jul. 9, 1998

Related U.S. Application Data

[60] Provisional application No. 60/054,770, Aug. 5, 1997.

[51] Int. Cl.$^6$ ...................................................... A61B 5/00
[52] U.S. Cl. ........................................... 600/585; 600/434
[58] Field of Search ..................................... 600/434, 435, 600/585; 604/264, 280

[56] References Cited

U.S. PATENT DOCUMENTS

| | | | |
|---|---|---|---|
| 3,485,234 | 12/1969 | Stevens . | |
| 4,000,739 | 1/1977 | Stevens . | |
| 4,169,464 | 10/1979 | Obrez . | |
| 4,925,445 | 5/1990 | Sakamoto et al. | 600/585 |
| 5,306,263 | 4/1994 | Voda | 600/435 |
| 5,312,341 | 5/1994 | Turi | 604/96 |
| 5,427,119 | 6/1995 | Swartz et al. | 600/585 |
| 5,800,413 | 9/1998 | Swartz et al. | 600/434 |
| 5,814,028 | 9/1998 | Swartz et al. | 600/435 |

FOREIGN PATENT DOCUMENTS

| | | |
|---|---|---|
| 755694 | 1/1997 | European Pat. Off. . |

OTHER PUBLICATIONS

Catheter Ablation of Accessory Atrioventricular Pathways in Young Patients: Use of Long Vascular Sheaths, the Transseptal Approach and a Retrograde Left Posterior Parallel Approach, Saul, et al., *Journal of American College of Cardiology*, vol. 21, No. 3, 1993.

"The Cordis Ducor Torque–Control Balloon Catheter", Jun., 1983.

*Primary Examiner*—Max Hindenburg
*Attorney, Agent, or Firm*—Cook, Alex, McFarron, Manzo, Cummings & Mehler

[57] ABSTRACT

A guiding catheter, including a specialized guiding catheter referred to as a guiding sheath, has a uniquely curved three-dimensional distal end portion. This distal end portion has a two-dimensional turn of less than a full circle, which turn includes both an incomplete turn section and a distal extension thereof which is an end section. The turn lies in three dimensions and, when viewed in a direction which moves distally along the curve, curves upwardly and downwardly and again upwardly, each out of the plane within which the rest of the catheter lies. The guiding catheter or sheath is especially useful for guiding an electrophysiology catheter for facilitating ablation within the right atrium and/or ablation within the left atrium, such as by way of a transsceptal procedure.

40 Claims, 2 Drawing Sheets

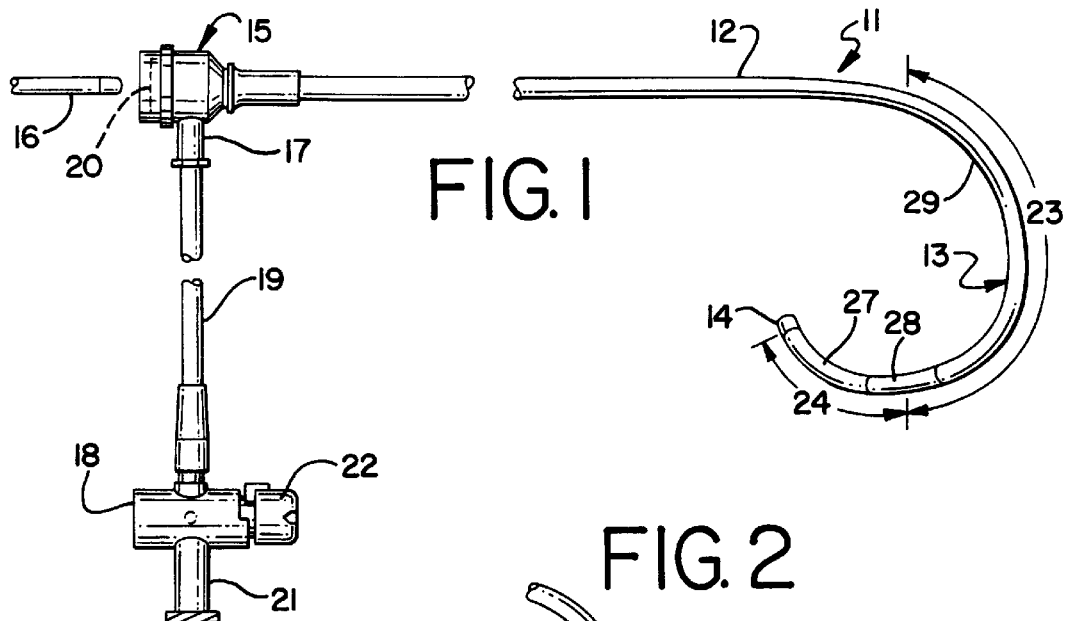
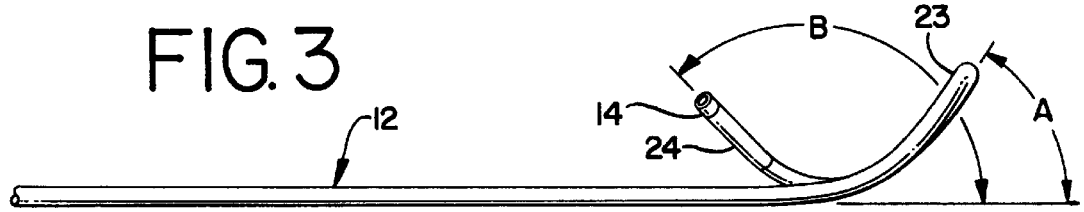

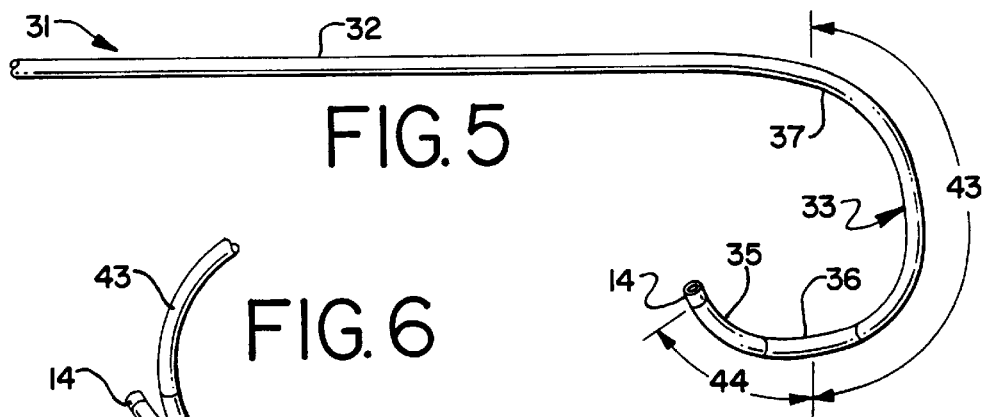
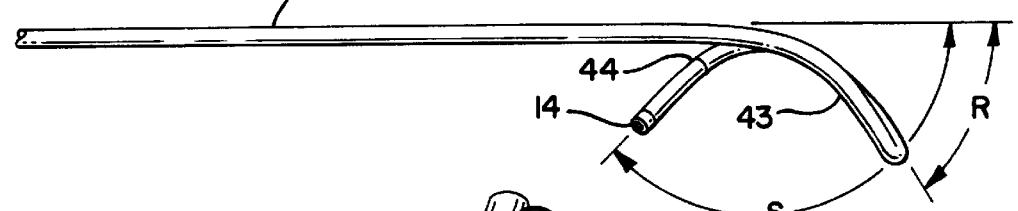
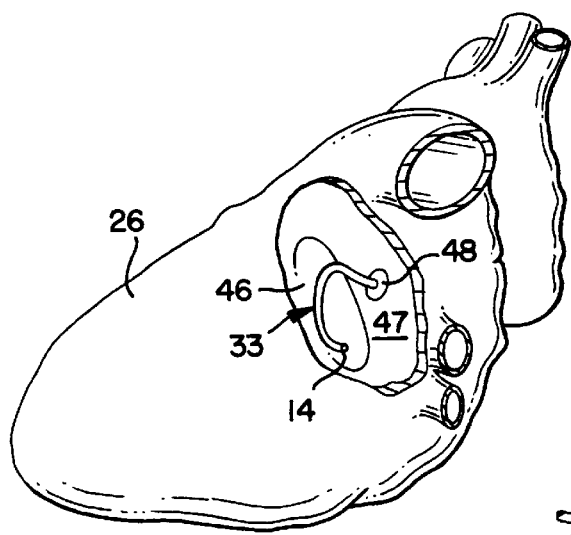
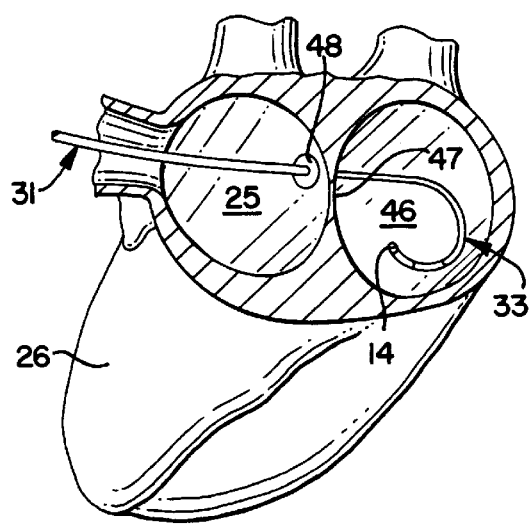

GUIDING SHEATH HAVING THREE-DIMENSIONAL DISTAL END

CROSS-REFERENCE TO RELATED APPLICATION

This application claims the benefit of U.S. provisional application Serial No. 60/054,770, filed Aug. 5, 1997.

BACKGROUND OF THE INVENTION

This invention generally relates to a guiding sheath which is especially suitable for guiding electrophysiology catheters. More particularly, a guiding catheter structure is provided which has a three-dimensional distal end which is particularly suitable for use during invasive cardiology procedures. One version of the guiding catheter curves in a direction especially suitable for posterior right use, while another version curves in a direction especially suitable for posterior left use. The latter configuration is especially suitable for transseptal procedures. The three-dimensional distal end is particularly useful in guiding an ablation catheter to direct its working distal end to the precise, desired location within the particular heart cavity being treated.

Guiding catheters are well known for use in providing a facilitating pathway for a treatment or diagnostic catheter. Often, such guiding catheters have shaped distal end portions which are useful in helping to properly locate the treatment or diagnostic catheter which passes therethrough. Often, the distal end portion of such a guiding catheter includes a bend or curve which can be generally characterized as two-dimensional. These types of curved or bent distal end portions generally lie within a single, two-dimensional plane, which plane also includes the elongated catheter shaft. A typical guiding catheter will include internal braiding in order to enhance pushability of the catheter through blood vessels and the like. Exemplary in this regard is Stevens U.S. Pat. No. 3,485,234, incorporated by reference hereinto.

Cannulas or sheath introducers are also generally known. Such devices have a passage therethrough for receiving a catheter and for guiding it during its initial stages of introduction into the body during a catheterization procedure. Often, these include hemostasis valving which takes the form of a self-sealing gasket. These introducer cannulas or sheaths can also include ports and side-tubes for introducing fluids and/or withdrawing fluids during various catheterization activities. Exemplary in this regard is Stevens U.S. Pat. No. 4,000,739, incorporated by reference hereinto. Sheath introducers typically follow a guidewire which had been introduced through a hollow needle during known procedures such as those which generally follow or modify the so-called Seldinger technique. Often, a guiding catheter is inserted through such a sheath introducer and into the blood vessel. Fernandez EP 755,694 shows a guiding catheter introducer assembly which includes an introducer sheath having a hemostasis valve, which sheath is attached or molded to a braided guiding catheter tubular body. This publication is incorporated by reference hereinto. Its distal end is shown to be generally straight or formed with a two-dimensional curve. The length of this guiding catheter is typical for guiding catheters, on the order of 100 cm so as to reach most locations within heart blood vessels.

Catheters having what can be characterized as a three-dimensional catheter distal end portion are generally known. An example in this regard is Obrez U.S. Pat. No. 4,169,464, incorporated by reference hereinto, which shows an angiographic catheter designed for selective catheterization of aortic branches such as various abdominal vessels. The three-dimensional shape of this catheter is particularly designed for facilitating such catheterization procedures.

Catheterization of the human heart at times necessitates having a catheter gain access to the atrium chambers. Generally speaking, access to the right atrium is gained through one of the femoral veins, typically the right femoral vein. Once a working catheter is within the right atrium, some procedures, such as ablation, require a pinpoint location of the catheter tip within the atrium cavity. At times, a guiding catheter having any of the known variety of curved distal ends, especially two-dimensional curved distal ends, does not provide the variation in movement which can be required and which can vary depending upon the needs of the procedure, the peculiarities of the patient, and the skill level of the cardiologist or other physician carrying out the procedure.

Similar pinpoint positioning requirements are encountered when attempting a catheterization procedure, such as an ablation, in the left atrium chamber. In addition, access to the left atrium is problematic. It is not possible to access the left atrium through the pulmonary artery, and access from the left ventricle is difficult. A typical approach for left atrium catheterization is a transseptal approach. With this known approach, access is gained through the right atrium by penetrating the interatrial septum. The transseptal approach is generally discussed in Mullins, "Transseptal Left Heart Catheterization: Experience With a New Technique in 520 Pediatric and Adult Patients", *Pediatric Cardiology*, 4:239–246, 1983; Saul et al, "Catheter Ablation of Accessory Atrioventricular Pathways in Young Patients: Use of Long Vascular Sheaths, the Transseptal Approach and a Retrograde Left Posterior Parallel Approach", *Journal of American College of Cardiology*, Vol. 21, No. 3, March, 1993, pp. 571–83; and Turi U.S. Pat. No. 5,312,341. Each of these is incorporated by reference hereinto.

Once access to the left atrium is attained by way of the transseptal approach, the difficulty remains in properly locating the treatment catheter tip, such as for an ablation procedure. As for a right atrium ablation, it is necessary to pinpoint a location for the ablation catheter treatment tip or the like. The location needed to be pinpointed could be within a difficult-to-access location along the inside wall of the atrium cavity. The arrhythmia to be controlled by ablation or the like can be at a location within the atrial cavity which cannot be readily accessed by the use of a straight guiding catheter or a guiding catheter having a heretofore known curved or bent distal end portion, including two-dimensional distal end curves. When eliminating accessory atrioventricular pathways by cardiac ablation techniques or the like, the pathway to be accessed can present a difficult maneuvering problem when using heretofore known guiding catheters. There is accordingly a need for a catheter-like guiding device which can be used in effecting pinpoint positioning of treatment or diagnostic catheters and the like, particularly when carrying out catheter cardiac ablation of the right atrium or of the left atrium by a transseptal procedure.

SUMMARY OF THE INVENTION

In accordance with the present invention, a guiding catheter is provided. Preferably the guiding catheter has the properties of both a guiding catheter and an introducer sheath. Such a guiding catheter is referred to herein as a guiding sheath. This guiding sheath includes a reinforced tubular body having a uniquely curved three-dimensional distal end portion. A hub is provided at the proximal end of the reinforced tubular body, the hub being characteristic of an introducer sheath type of device, typically including a hemostasis valve arrangement. In this manner, a working catheter, typically an electrophysiology catheter, is fed through the hub, the reinforced body and out the distal tip of the guiding sheath in accordance with the invention. The three-dimensional distal end portion of the guiding catheter of the invention is suited for facilitating pinpoint guidance of the working catheter distal end to a desired location during an invasive cardiology procedure. The guiding catheter is especially well suited for facilitating ablation within the right atrium and/or ablation within the left atrium, such as by way of a transseptal procedure.

It is accordingly a general object of the present invention to provide an improved guiding catheter or guiding sheath having a three-dimensional distal end portion.

Another object of the present invention is to provide an improved guiding catheter or guiding sheath, method of making, and procedure of use which are especially well suited for a catheter system including a working catheter, the catheter system being for invasive cardiology procedures which present particularly challenging positioning problems.

Another object of this invention is to provide an improved guiding catheter or guiding sheath having a three-dimensionally shaped distal end portion which is well suited for guiding an ablation catheter to a desired ablation site within the right atrium.

Another object of this invention is to provide an improved guiding catheter having a distal end portion to which the plastic memory of a three-dimensional shape has been imparted and which is well suited for guiding an ablation catheter to a desired ablation site within the left atrium, such being by way of the right atrium, including passage through the interatrial septum.

Another object of the present invention is to provide an improved electrophysiology guiding sheath or catheter and electrophysiology catheter system for carrying out invasive cardiology procedures, including catheter cardiac ablation for eliminating accessory atrioventricular pathways and for controlling arrhythmia within a heart chamber.

Another object of this invention is to provide an improved system including a guiding sheath or catheter to direct the ablation tip of a treatment catheter toward the posterior lateral to lateral section of the tricuspid valve, as well as the related procedure.

Another object of this invention is to provide an improved system having a guiding sheath or catheter for directing the ablation tip of a treatment catheter toward the posterior lateral to posterior septal region of the mitral valve, as well as the related procedure.

These and other objects, features and advantages of the present invention will be apparent from and clearly understood through a consideration of the following detailed description.

BRIEF DESCRIPTION OF THE DRAWINGS

In the course of this description, reference will be made to the attached drawings, wherein:

FIG. 1 is a side elevational view of a catheter system having an ablation catheter and a guiding sheath having a three-dimensional distal end portion which is particularly suitable for use in the right atrium;

FIG. 2 is an end elevational view showing a portion of the distal end area of the guiding sheath of FIG. 1;

FIG. 3 is a top plan view, partially broken away, of the guiding sheath of FIGS. 1 and 2;

FIG. 4 is a somewhat diagrammatic perspective view illustrating a position of the guiding sheath of FIGS. 1, 2 and 3 within the right atrium of a human heart;

FIG. 5 is an elevational view, partially broken away, of a guiding sheath according to the invention which is especially suitable for use in the left atrium;

FIG. 6 is an end elevational view, partially broken away, of the guiding sheath shown in FIG. 5;

FIG. 7 is a top plan view, partially broken away, of the guiding sheath of FIGS. 5 and 6;

FIG. 8 is a somewhat diagrammatic, perspective view of a human heart showing a portion of the guiding sheath of FIGS. 5, 6 and 7 transseptally positioned within the left atrium of a human heart; and FIG. 9 is a somewhat schematic cross-section through FIG. 8, showing the guiding sheath after having passed through the right atrium, through the septum, and into the left atrium.

DESCRIPTION OF THE PREFERRED EMBODIMENTS

The guiding sheath in accordance with this invention is generally illustrated at 11 in FIG. 1. Guiding sheath 11 incorporates a reinforced tubular body 12, which has a three-dimensional distal end portion, generally designated at 13. The distal end portion has its three-dimensional shape by virtue of memory imparted to it during a forming procedure. This three-dimensional shape is plastic to the extent it can be temporarily modified, even to the extent of being substantially straightened, such as by a guidewire passing partially or entirely therethrough. A soft tip 14 is provided at the remote distal end of the three-dimensional distal end portion 13. A hub assembly, generally designated at 15, is positioned at the proximal end of the reinforced tubular body 12.

Preferably, the hub assembly 15 includes a hemostasis valve 20 of generally known configuration and positioning within the hub assembly. With this arrangement, an operational or working catheter of known structure, function and operation, typically an ablation catheter 16 (partially shown in FIG. 1), passes into the hub assembly 15, through the hemostasis valve when positioned therewithin, and into and through the reinforced tubular body 12. At proper times during a cardiology procedure, the operating catheter continues to progress therethrough until it exits through the soft tip 14.

A side port 17 is preferably included for joining a stop cock assembly 18 by way of tubing 19. In the illustrated embodiment, at least one side port 21 is provided for connection such as by way of a Leur lock assembly. Access through the stop cock assembly is gained by manipulation of a lever 22. It is also possible to include multiple ports in the stop cock assembly. The stop cock assembly is useful for passing liquid for flushing or other delivery purposes and/or for withdrawing fluids as needed, either in series or simultaneously. When used as a guiding catheter, the device can omit or modify the hub assembly or stop cock assembly in accordance with the knowledge in the art.

Referring more particularly to the three-dimensional distal end portion 13, a primary portion of same in the illustrated embodiments is a single incomplete turn section 23. When viewed in two-dimensional space, within a plane generally passing through the reinforced tubular body 12, same has a generally U-shaped configuration. This view in two-dimensional space can be considered as a projection of the incomplete turn section 23 upon the plane along which the tubular body 12 generally lies (hereinafter the "first" plane, which coincides with the plane of the paper as in FIG. 1 and FIG. 5).

In addition, this incomplete turn section 23 has a third dimensional orientation which generally lies along a plane (a "second" plane) which intersects the aforesaid first plane at an acute angle A, this shape component of turn section 23 being generally shown in FIG. 3. It will be appreciated from this FIG. 3 view that this third dimensional orientation need not strictly lie along the acutely angled plane, or second plane, but it can include a slight bow as shown in FIG. 3, a generally concave bow being shown.

Located distally of the three-dimensional incomplete turn 23 is an end section 24. This also has three-dimensional attributes. When viewed in two dimensions, namely along (or as a projection upon) the plane of the tubular body 12 (the first plane as seen in FIG. 1), this component generally continues with the curve of the single incomplete turn section 23, except the curvature can be somewhat tighter, as illustrated in FIG. 1, particularly at the proximalmost portion of the distal end section 24.

When viewed in the third dimension, as generally illustrated in FIG. 3, the end section 24 has a third dimensional orientation. When thus viewed, the end section 24 roughly follows another plane (a "third" plane) which intersects the first plane passing through the tubular body 12 (as seen in FIG. 1). This planar intersection is at an obtuse angle B (FIG. 3), which obtuse angle is defined with an orientation consistent with that of the acute angle A. Similar to the third dimensional component of the incomplete turn section, the third dimensional component of the end section 24 can be bowed with respect to the plane generally defined at angle B, a generally concave bow being shown at the length distal of the transition between the incomplete turn section 23 and the end section 24. However, at its most distal end, the curve can be very gradual, or even substantially straight in this third dimension, as illustrated in the FIG. 3 embodiment.

The embodiment of the invention which is illustrated in FIG. 1 through FIG. 4 is especially suitable for use within the right atrium. FIG. 4 generally illustrates entry of the guiding sheath 11 after same has been positioned within right atrium 25 of a human heart 26. When a working catheter 16 such as an ablation catheter is passed through and out of the soft tip 14, manipulation at the proximal end, such as by rotation of the hub assembly 15, causes the three-dimensional distal end portion 13 to be positioned as desired and in a manner which is advantageously responsive to these types of proximal-portion manipulations.

FIG. 5 shows a guiding sheath 31 having a reinforced tubular body 32 and a three-dimensional distal end portion, generally designated at 33, which portion 33 has a configuration having the same overall characteristics as three-dimensional distal end portion 13, except the respective third dimensional components are oppositely oriented. The two-dimensional component of this distal end portion configuration, that is the component lying in a first plane also containing the reinforced tubular body 32, is similar in configuration to the FIG. 1–FIG. 4 embodiment. This is perhaps best seen by comparing FIG. 5 with FIG. 1.

Referring more particularly to the differences between the FIG. 1 embodiment and the FIG. 5 embodiment, the three-dimensional incomplete turn section 43 curves in a direction generally opposite to the three-dimensional incomplete turn section 23. This difference is evident by comparing FIG. 6 with FIG. 2 and by comparing FIG. 7 with FIG. 3. It will be noted that acute angle R of the second embodiment is oriented generally along a second plane in a direction away from or opposite to acute angle A of the first embodiment, each angle being defined in relationship to the first plane passing through the tubular body. Also, the distally located three-dimensional end section 44 of the second embodiment generally lies along the plane (the third plane) intersecting the plane of the tubular body 32 (the first plane) by an obtuse angle S. Obtuse angle S is oriented in a direction generally opposite to that of obtuse angle B of the first embodiment.

It will be appreciated that the three-dimensional incomplete turn section 43 does not lie precisely along the second plane generally illustrated with angle R. Instead, there is a bow or gradual curving as can be seen in the drawings. Also, the three-dimensional end section 44 does not lie precisely along the third plane designated by means of the obtuse angle S. Instead, end section 44 displays a bowed characteristic, as is evident from the drawings. A somewhat concave curve, bowed inwardly, is shown. Distalmost portion of end section 44 can be approximately or substantially straight in this illustrated third dimension.

FIG. 8 illustrates a human heart 26, viewed from an angle generally behind that shown in FIG. 4. The cutaway portion exposes the left atrium 46. Also shown is the interatrial septum 47. The overall relationship among the right atrium 25, the left atrium 46 and the interatrial septum 47 can also be appreciated from FIG. 9.

With further reference to the transseptal procedure for gaining accessing to and for catheterization of the left atrium 46, a transseptal needle (not shown) is transluminally fed into the right atrium 25 in a generally known manner. A transseptal puncture is then performed, typically through the fossa ovalis 48 of the interatrial septum 47. Thereafter, by conventional techniques and with the aid of a guidewire, the guiding sheath 31 is passed through the puncture made through the fossa ovalis, after which the three-dimensional distal end portion 33 enters the left atrium 46. Thereafter, the working catheter 16 is passed through the guiding sheath 31, permitting the cardiologist to perform the desired procedure, such as ablation, after specifically pinpointing the treatment location by manipulation of the guiding sheath as generally discussed herein.

Referring more particularly to the construction of the tubular body 12, 32 of the guiding sheath 11, 31, it will have a reinforced characteristic so as to exhibit adequate torsional responsiveness and column strength in order to suitably perform as a guiding catheter, as well as a sheath introducer. Elimination or minimization of kinking is also an important objective. Typically, these reinforcing functions are accomplished by the inclusion of braiding, such as of a continuous metal or polymeric coil positioned within or embedded within the walls of the guiding sheath. Also, selection of materials for the walls of the tubular body, including polymer coextrusion approaches, which include relatively stiff extrusion layer(s), can also address the need for this reinforced attribute.

It is generally preferred to provide the reinforced tubular body 12, 32 with stiffness variation along its length. In this regard, the least stiff or softest component is typically the soft tip 14. Subsequent sections, moving in the proximal direction therefrom preferably exhibit increasing stiffness characteristics. Thus, in the illustrated embodiment, a distal section 27, 35 has a Durometer hardness which is greater than or harder than the soft tip 14. An intermediate section 28, 36 is harder or stiffer than the distal section 27, 35. A proximal section 29, 37 is harder than the intermediate section. In the illustrated embodiment, this proximal section is the section of greatest stiffness. Exemplary materials include nylons and polyamides, including polyamide materials which are copolymers and include structural components in addition to amide groups. These materials are available in varying Durometer hardness values, thereby facilitating desired hardness selections.

In an important aspect of the invention, the hubbed guiding sheath in accordance with the invention combines the three-dimensional distal end portion 13, 33, as generally discussed herein, with an overall length which is relatively short for a typical guiding catheter. This relative shortness contributes to the defining of the device as a guiding sheath. A typical lumen length for a guiding sheath in accordance with the invention is between about 60 cm and about 70 cm. A typical guiding sheath will be of a so-called 8 French size; that is, it will allow for passage therethrough of an 8 French working catheter. A typical inner diameter for the guiding sheath is 0.11 inch, and a typical outer diameter is 0.13 inch.

The three-dimensional distal end portion 13, 33 is formed by generally conventional techniques. The tubing is placed over a forming wire having the desired three-dimensional shape. Thereafter, heating, such as by placing the wire-supported tubing in boiling water for about three minutes, softens the polymers. Preferably, the assembly is then withdrawn from the heat and subjected to a thermal shock, such as by contacting with ice water. As is generally known, this results in molecular reorientation as the polymer rapidly solidifies to impart to the polymer a memory of the described shape of the three-dimensional distal portion. Thereafter, the forming wire is removed, after which the shape of the three-dimensional distal portion returns due to the memory of the forming wire shape which was imparted to the polymer of the distal portion.

It will be understood that the embodiments of the present invention which have been described are illustrative of some of the applications of the principles of the present invention. Numerous modifications may be made by those skilled in the art without departing from the true spirit and scope of the invention.

We claim:

1. A guiding sheath comprising:
   a tubular body member having a proximal end portion and a distal end portion;
   said distal end portion has a three-dimensional shape, said three-dimensional shape of the distal end portion includes the combination of a three-dimensional incomplete turn section and of a three-dimensional end section which is coextensive with and distal of said incomplete turn section;
   said incomplete turn section and said end section together project onto a two-dimensional first plane as a turn of less than a full circle;
   said three-dimensional incomplete turn section also has a third dimension within which said turn of less than a full circle curves upwardly and then downwardly when viewed in a direction which moves distally along said incomplete turn section of the distal end portion of the tubular body member; and
   said three-dimensional end section has a third dimension within which said turn of less than a full circle again curves upwardly at a location distal of the location at which said turn of less than a full circle curves downwardly.

2. The guiding sheath in accordance with claim 1, wherein said turn of less than a full circle curves upwardly and then downwardly generally along a second plane which intersects said first plane at an acute angle.

3. The guiding sheath in accordance with claim 2, wherein said turn of less than a full circle again curves upwardly along a third plane which intersects said first plane at an obtuse angle defined at an orientation which is the same as that of said acute angle.

4. The guiding sheath in accordance with claim 1, further including a hub assembly at the proximal end of said proximal end portion of the tubular body, and said hub assembly includes a hemostasis valve.

5. The guiding sheath in accordance with claim 4, wherein said hub assembly includes a side port in fluid-passing communication with a stop cock assembly for delivery or withdrawal of fluids through said guiding sheath.

6. The guiding sheath in accordance with claim 1, wherein said proximal end portion has column strength attributes of an introducer sheath, these attributes being imparted at least in part by braiding within said proximal end portion.

7. The guiding sheath in accordance with claim 1, wherein said distal end portion has shape memory attributes of a guiding catheter distal end portion, these memory attributes permitting general straightening of said turn of less than a full circle by a guidewire passing therethrough, the memory attributes further providing for return, during removal of the guidewire, of said three-dimensional shape of the turn of less than a full circle.

8. The guiding sheath in accordance with claim 2, wherein said turn of less than a full circle is bowed with respect to said second plane when same curves upwardly and downwardly.

9. The guiding sheath in accordance with claim 2, wherein said turn of less than a full circle is bowed, in a concave manner, with respect to said second plane when same curves upwardly and downwardly.

10. The guiding sheath in accordance with claim 3, wherein said turn of less than a full circle is bowed with respect to said third plane when same curves upwardly.

11. The guiding sheath in accordance with claim 3, wherein said turn of less than a full circle is bowed, in a concave manner, with respect to said third plane when same curves upwardly.

12. The guiding sheath in accordance with claim 10, wherein a distal end length which is distal of the bowed length is substantially straight along said third plane.

13. The guiding sheath in accordance with claim 1, wherein said turn of less than a full circle curves in a direction suitable for use within the right atrium of a human heart.

14. The guiding sheath in accordance with claim 1, wherein said turn of less than a full circle curves in a direction suitable for use within the left atrium of a human heart, said turn being oriented opposite to that which would be suitable for use within the right atrium.

15. The guiding sheath in accordance with claim 1, wherein said guiding sheath has a lumen therethrough, and the length of said lumen is between about 60 cm and about 70 cm.

16. The guiding sheath in accordance with claim 1, wherein said guiding sheath has an inner lumen throughout its elongated proximal end portion and distal end portion, a soft tip is positioned at the distalmost location of said distal end portion, said soft tip has a Durometer hardness substantially softer than the Durometer hardness of the elongated proximal end portion, and said distal end portion includes at least one intermediate length between said elongated proximal end portion and said soft tip, said intermediate length having a Durometer hardness intermediate that of said soft tip and of said elongated proximal end portion.

17. A guiding sheath comprising:
a tubular body member having an elongated proximal end portion and a distal end portion which is shorter than said elongated proximal end portion;
said distal end portion has a three-dimensional shape, said three-dimensional shape of the distal end portion includes the combination of a three-dimensional incomplete turn section and of a three-dimensional end section which is coextensive with and distal of said incomplete turn section;
said incomplete turn section and said end section together project onto a first plane as a two-dimensional turn of less than a full circle;
said three-dimensional incomplete turn section has a third dimension within which said turn of less than a full circle curves upwardly and then downwardly generally along a second plane which intersects said first plane at an acute angle; and
said three-dimensional end section has a third dimension within which said turn of less than a full circle again curves upwardly generally along a third plane which intersects said first plane at an obtuse angle.

18. The guiding sheath in accordance with claim 17, wherein said obtuse angle is defined with an orientation consistent with that of said acute angle.

19. The guiding sheath in accordance with claim 17, wherein said turn of less than a full circle is bowed with respect to said second plane when same curves upwardly and downwardly.

20. The guiding sheath in accordance with claim 17, wherein said turn of less than a full circle is bowed with respect to said third plane when same curves upwardly.

21. The guiding sheath in accordance with claim 20, wherein a distal end length which is distal of the bowed length is substantially straight along said third plane.

22. A guiding sheath having properties of both a guiding catheter and of an introducer sheath, the guiding sheath comprising:
a tubular body member having a proximal end portion and a distal end portion, said proximal end portion has a column strength attribute of an introducer sheath, and said distal end portion has a catheter-guiding attribute of a guiding catheter;
said distal end portion has a memory of a three-dimensional shape imparted to the distal end portion, said three-dimensional shape of the distal end portion includes the combination of a three-dimensional single incomplete turn section and of a three-dimensional end section which is coextensive with and distal of said single incomplete turn section;
said single incomplete turn section and said end section together project onto a two-dimensional plane as a turn of less than a full circle;
said three-dimensional single incomplete turn section also has a third dimension within which said turn of less than a full circle curves upwardly and then downwardly when viewed in a direction which moves distally along said distal end portion of the tubular body member; and
said three-dimensional end section has a third dimension within which said turn of less than a full circle curves upwardly at a location closely distal of the location at which said turn of less than a full circle curves downwardly.

23. The guiding sheath in accordance with claim 22, wherein said turn of less than a full circle curves upwardly and then downwardly generally along a second plane which intersects said first plane at an acute angle.

24. The guiding sheath in accordance with claim 23, wherein said turn of less than a full circle again curves upwardly along a third plane which intersects said first plane at an obtuse angle defined at an orientation which is the same as that of said acute angle.

25. The guiding sheath in accordance with claim 24, wherein said turn of less than a full circle is bowed, in a concave manner, with respect to said second plane when same curves upwardly and downwardly.

26. The guiding sheath in accordance with claim 25, wherein said turn of less than a full circle is bowed, in a concave manner, with respect to said third plane when same curves upwardly.

27. The guiding sheath in accordance with claim 26, wherein a distal end length which is distal of the bowed length is substantially straight along said third plane.

28. A catheter system, comprising:
a working catheter for heart catheterization, said working catheter having a tubular body of a known outer diameter;
a guiding sheath having a tubular body member with a selected inner diameter which is larger than said known outer diameter of the working catheter;
said tubular body member of the guiding sheath has a proximal end portion and a distal end portion, said proximal end portion has a column strength attribute of an introducer sheath, and said distal end portion has a catheter-guiding attribute of a guiding catheter;
said distal end portion has a three-dimensional shape, said three-dimensional shape of the distal end portion of the guiding sheath includes the combination of a three-dimensional incomplete turn section and of a three-dimensional end section which is coextensive with an distal of said incomplete turn section;
said incomplete turn section and said end section together project onto a first plane as a two-dimensional turn of less than a full circle;
said three-dimensional incomplete turn section also has a third dimension within which said turn of less than a full circle curves upwardly and then downwardly when viewed in a direction which moves distally along said distal end portion of the tubular body member of the guiding sheath; and
said three-dimensional end section has a third dimension within which said turn of less than a full circle curves upwardly at a location distal of the location at which said turn of less than a full circle curves downwardly.

29. The catheter system in accordance with claim 28, wherein said working catheter is an electrophysiology catheter for carrying out ablation procedures.

30. The catheter system in accordance with claim 28, wherein said turn of less than a full circle curves upwardly and then downwardly generally along a second plane which intersects said first plane at an acute angle.

31. The catheter system in accordance with claim 30, wherein said turn of less than a full circle again curves upwardly along a third plane which intersects said first plane at an obtuse angle defined at an orientation which is the same as that of said acute angle.

32. The catheter system in accordance with claim 30, wherein said turn of less than a full circle curve is bowed with respect to said second plane.

33. The catheter system in accordance with claim 31, wherein said turn of less than a full circle curve is bowed with respect to said third plane.

34. The catheter system in accordance with claim 33, wherein a distal end length which is distal of the bowed length is substantially straight along said third plane.

35. The catheter system in accordance with claim 28, wherein said guiding sheath has a lumen therethrough, and the length of said lumen is between about 60 cm and about 70 cm.

36. The catheter system in accordance with claim 28, wherein said guiding sheath has an inner lumen throughout its elongated proximal end portion and distal end portion, a soft tip is positioned at the distalmost location of said distal end portion, said soft tip has a Durometer hardness substantially softer than the Durometer hardness of the elongated proximal end portion, and said distal end portion includes at least one intermediate length between said elongated proximal end portion and said soft tip, said intermediate length having a Durometer hardness intermediate that of said soft tip and of said elongated proximal end portion.

37. A guiding catheter comprising:

a tubular body member having an elongated proximal end portion and a distal end portion which is shorter in length than said elongated proximal end portion;

said distal end portion has a memory of a three-dimensional shape imparted to the distal end portion, said three-dimensional shape of the distal end portion includes the combination of a three-dimensional incomplete turn section and of a three-dimensional end section which is coextensive with and distal of said incomplete turn section;

said incomplete turn section and said end section together project onto a first plane as a two-dimensional turn of less than a full circle;

said three-dimensional incomplete turn section also has a third dimension within which said turn of less than a full circle curves upwardly and then downwardly, when viewed in a direction which moves distally along said distal end portion of the tubular body member, generally along a second plane which intersects said first plane at an acute angle; and said three-dimensional end section has a third dimension within which said turn of less than a full circle curves upwardly at a location distal of the location at which said turn of less than a full circle curves downwardly and generally along a third plane which intersects said first plane at an obtuse angle, said obtuse angle being defined with an orientation consistent with that of said acute angle.

38. The catheter system in accordance with claim 37, wherein said turn of less than a full circle curve is bowed with respect to said second plane.

39. The catheter system in accordance with claim 37, wherein said turn of less than a full circle curve is bowed with respect to said third plane.

40. The catheter system in accordance with claim 39, wherein a distal end length which is distal of the bowed length is substantially straight along said third plane.

* * * * *